United States Patent [19]
McClure et al.

[11] Patent Number: 5,718,242
[45] Date of Patent: *Feb. 17, 1998

[54] CARDIAC ARRHYTHMIA DETECTION SYSTEM FOR AN IMPLANTABLE STIMULATION DEVICE AND METHOD

[75] Inventors: Kelly H. McClure, Simi Valley; Gene A. Bornzin, Camarillo, both of Calif.

[73] Assignee: Pacesetter, Inc., Sylmar, Calif.

[ * ] Notice: The term of this patent shall not extend beyond the expiration date of Pat. No. 5,560,369.

[21] Appl. No.: 670,946

[22] Filed: Jun. 26, 1996

Related U.S. Application Data

[60] Division of Ser. No. 310,688, Sep. 22, 1994, Pat. No. 5,560,369, which is a continuation-in-part of Ser. No. 984,157, Dec. 1, 1992, abandoned.

[51] Int. Cl.$^6$ .................. A61B 5/0456; A61N 1/365
[52] U.S. Cl. .................. 128/704; 128/705; 607/14
[58] Field of Search .................. 128/696, 697, 128/704, 705, 708; 607/4, 5, 14, 27

[56] References Cited

U.S. PATENT DOCUMENTS

| | | | |
|---|---|---|---|
| 3,554,187 | 1/1971 | Glassner et al. | 128/703 |
| 3,978,856 | 9/1976 | Michel | 128/703 |
| 5,086,772 | 2/1992 | Lanard et al. | 607/4 |
| 5,273,049 | 12/1993 | Steinhaus et al. | 128/696 |
| 5,330,507 | 7/1994 | Schwartz | 128/705 X |
| 5,560,369 | 10/1996 | McClure et al. | 128/704 |

Primary Examiner—Jeffrey R. Jastrzab

[57] ABSTRACT

A cardiac event and arrhythmia detection system and method detects arrhythmic cardiac activity or other information from an electrogram signal of a heart. The system senses the electrogram signal through an electrogram lead, preliminarily processes the signal, and converts it to a plurality of discrete digital signals, each of which represents the magnitude of the electrogram signal at a prescribed sample time. The discrete digital signals are applied to both a cardiac event detector and a morphology detector. The morphology detector detects selected changes in the morphology (shape) of the electrogram signal, wherein such changes automatically control the sensitivity (gain and/or threshold) used to detect cardiac events. The occurrence of a prescribed amount of change in the detected morphology over time indicates the occurrence of a prescribed arrhythmic cardiac condition.

8 Claims, 6 Drawing Sheets

CARDIAC ARRHYTHMIA DETECTION SYSTEM FOR AN IMPLANTABLE STIMULATION DEVICE AND METHOD

CROSS-REFERENCE TO RELATED APPLICATIONS

This is a divisional of application(s) Ser. No. 08/310,688 filed on Sep. 22, 1994, now U.S. Pat. No. 5,560,369, which is a continuation-in-part of application Ser. No. 07/984,157, filed Dec. 1, 1992, now abandoned.

FIELD OF THE INVENTION

The present invention relates to a cardiac arrhythmia detection system for use in an implantable stimulation device, such as an implantable pacemaker, cardioverter or a defibrillator. More particularly, the present invention relates to a system for detecting and tracking cardiac events and electrogram morphology so that the transition between rhythmic activity to arrhythmic activity can be detected. The present invention further includes an improved implantable cardiac event detection system which eliminates double sensing of T-waves.

BACKGROUND OF THE INVENTION

The major pumping chambers in the human heart are the left and right ventricles. The simultaneous physical contraction of the myocardial tissue in these chambers expels blood into the aorta and the pulmonary artery. Blood enters the ventricles from smaller antechambers called the left and right atria which contract about 100 milliseconds (ms) before the ventricles. This interval is known as the atrio-ventricular (AV) delay. The physical contractions of the muscle tissue result from the depolarization of such tissue, which depolarization is induced by a wave of spontaneous electrical excitation which begins in the right atrium, spreads to the left atrium and then enters the AV node which delays its passage to the ventricles via the so-called bundle of His. The frequency of the waves of excitation is normally regulated metabolically by the sinus node. The atrial rate is thus referred to as the sinus rate or sinus rhythm of the heart.

Electrical signals corresponding to the depolarization of the myocardial muscle tissue appear in the patient's electrocardiogram. A brief low amplitude signal known as the P-wave accompanies atrial depolarization normally followed by a much larger amplitude signal, known as the QRS complex, with a predominant R-wave signifying ventricular depolarization. Repolarization prior to the next contraction is marked by a broad waveform in the electrocardiogram known as the T-wave.

A typical implanted cardiac pacer (or pacemaker) operates by supplying missing stimulation pulses through an electrode on a pacing lead in contact with the atrial or ventricular muscle tissue. The electrical stimulus independently initiates depolarization of the myocardial (atrial or ventricular) tissue resulting in the desired contraction. The P-wave or R-wave can be sensed through the same lead (i.e., the pacing lead) and used as a timing signal to synchronize or inhibit stimulation pulses in relation to spontaneous (natural or intrinsic) cardiac activity. The sensed P-wave or R-wave signals are referred to as an atrial electrogram or ventricular electrogram, respectively.

Note that the term electrogram lead is used herein to refer to the lead that transmits the sensed electrogram signal from the heart, and the term pacing lead is used to refer to the lead that transmits the stimulation pulse to the heart. As mentioned above, however, these "leads" are generally combined (i.e., the sensed electrogram signal is transmitted from the heart by the same lead that transmits the stimulation pulse to the heart). The separate terms "electrogram lead" and "pacing lead" are used herein merely to indicate that the electrogram signal and the stimulation pulse could be transmitted using separate leads.

Every modern-day implantable pacemaker includes a sensing circuit, whether the activity of one or both chambers of the heart are sensed. A cardiac event is sensed when an amplified electrogram signal exceeds a threshold value. If the sensitivity level is too low (i.e., the gain is too low), then some cardiac events will not be sensed because even peak signals may not exceed the threshold level. If the sensitivity level is too high, on the other hand, the high gain of the amplifier may cause noise or T-wave signals to be sensed, giving rise to erroneous sensing of cardiac events. Pacemakers provided with communications telemetry (e.g., noninvasive programming capabilities) advantageously allow the physician to set the sensitivity level.

There are at least two disadvantages to having the physician set the sensitivity level. First, adjusting the sensitivity level is one more thing that the physician must remember to do, and it would be advantageous to relieve him or her of that task if it is possible to do so. Second, and more important, the physician generally sees the patient only occasionally, and weeks or months may go by without the sensitivity level being changed. Problematically, the sensitivity level that will accurately detect cardiac events at a given threshold level for a patient does not stay static; both R-wave amplitude and frequency content can vary considerably within a given patient. Changes in the sensitivity level are needed to accommodate for physical and mental stress. In addition, the sensitivity level needs to change as myocardial tissue (heart muscle tissue) undergoes scarring or other physical responses to the implanted electrogram lead (s). Other changes in the myocardium-electrogram lead interface, e.g., shifting of the position of the electrogram lead, may also cause changes in the proper sensitivity level.

Unfortunately, these changes occur over a period of days and, in some cases, even hours or minutes. Because the physician generally sees the patient only every few weeks or months, the pacemaker sensing circuits can erroneously detect, or not detect, cardiac events over large periods of time. This erroneous detection/non-detection can cause under-pacing or over-pacing of the heart. Unfortunately for the patient, such changes may potentially leave him or her in a worse condition than he or she was in before the pacemaker was implanted. At best, the pacemaker is not able to operate efficiently—either by unnecessarily pacing and thereby draining the battery and risking pacemaker-induced tachycardias; or by not pacing as often as is needed by the patient. Thus, what is needed is a way to adjust the sensitivity level of a cardiac event detector in response to changing conditions in an electrogram signal over a short period of time.

One way of adjusting the sensitivity level of a cardiac event detector is discussed in U.S. Pat. No. 4,708,144 issued to Hamilton et al. The Hamilton et al. patent shows the use of an attenuator to attenuate an amplified signal before such signal is digitized and rectified. After the signal is digitized and rectified, the signal is connected to a digital comparator. The digital comparator compares each digitized and rectified sample to a threshold value. If the digitized and rectified sample exceeds the threshold value, a cardiac event is detected. In response to the detected cardiac event, a pacemaker control circuit takes appropriate action.

Each digitized and rectified sample is also presented to a peak detector which stores the maximum, or largest, digitized and rectified sample. The stored maximum sample is coupled to the pacemaker control circuit. After each cardiac event is sensed, the pacemaker control circuit averages the stored maximum with any of the previously occurring maximums yielding an average peak value. This average peak value is used to determine whether or not the attenuator should be adjusted to increase or decrease the attenuation provided by the attenuator. Specifically, if the average peak value increases, the attenuation is increased; and if the average peak value decreases, the attenuation is decreased, thereby adjusting the amplitude of the signal before it is digitized and rectified.

Disadvantageously, even though the Hamilton et al. circuit provides one technique for dynamically adjusting the sensitivity level of a cardiac event detector, by attenuating the cardiac signals after the amplification stage, it suffers from potentially clipping the input signal before even reaching the attenuation stage or the peak detecting stage. Furthermore, it completely lacks the ability to eliminate the sensing of high amplitude T-waves, which could cause the peak detector to erroneously detect the peak T-wave. Furthermore, if the amplitude of the T-wave is too high, or if the gain of the amplifier is so high that the R-wave is clipped and the T-wave is, by comparison, similar in amplitude to the clipped R-wave, it can result in "double sensing". Double sensing, when it occurs, then falsely indicates that a tachycardia is present. Thus, Hamilton et al. is not suitable for important cardiac monitoring functions beyond merely sensing a cardiac event. What is needed is a system which adjusts the gain at the pre-amplification stage for an optimum signal (i.e., without clipping the input signal) and then reliably eliminate sensing of the T-wave.

In addition to the detection of cardiac events, it is desirable, in the treatment of certain heart ailments, or for the detection of such ailments, to continuously monitor the patient over a certain period of time in order to determine the effectiveness of the treatment being administered by a pacemaker, under different conditions of stress or varying conditions of the heart. If the sensing circuit detects that the pacemaker is administering a less than ideal, or optimum, treatment, the treatment can be adjusted (e.g., by increasing or decreasing the rate at which pacing pulses are delivered, by decreasing the threshold level of the threshold detector, or by increasing the amplitude or duration of the pacing pulse).

Unfortunately, events that would indicate that the pacemaker may be providing less than the optimum treatment may occur only infrequently. Thus, a physician may not detect such abnormal events during a weekly, biweekly or monthly examination, which may last only a few minutes and may not be able to adjust the pacemaker accordingly. In an effort to solve this problem, data acquisition systems have been developed that record electrogram signals over a predetermined period of time, e.g., on the order of days. The electrogram signals may then be analyzed by a physician or, in more advanced system, by a microcontroller in the pacemaker in accordance with a control program that is designed to react to various conditions that are manifested by the electrogram signals. Such data acquisition systems advantageously allow detailed analysis of the electrogram signal over long periods of time thereby facilitating the detection and accommodation of infrequent heart abnormalities or the early detection of slowly developing heart ailments. Such long-term monitoring, particularly where implemented in advanced programmed systems, makes possible the purposeful and possibly automatic treatment of heart abnormalities long before the actual failure of a pacemaker to properly service the heart. In addition, with such automated systems, therapies, such as antitachycardia pacing and defibrillation, can be performed on the heart by pacing systems or dedicated defibrillators that would otherwise not be able to be performed as quickly or automatically.

Unfortunately, implanted data acquisition systems have heretofore only been operable over a limited sample of the electrogram signal. This is because such systems store the electrogram signal in a memory. The memory is of a limited size, and when the memory is full, either part of the previously recorded electrogram signal must be discarded to make room for new electrogram signal to be recorded, or the data acquisition system must stop recording. In an effort to solve this problem, various high capacity means of storing electrogram signals have been developed such as magnetic tape recording systems. For example, U.S. Pat. No. 4,250,888 issued to Grosskopf, suggests that when the memory is full, a warning message be given that alerts the patient to the need to contact the physician or to activate a tape recording system at home.

Disadvantageously, the Grosskopf approach may require that the patient report to a potentially inconvenient location, (i.e., the physician's office or the patient's home where the tape recording system is located). Such inconvenience may encourage the patient to ignore the warning message. In addition, the warning message can be intrusive and embarrassing. Furthermore, such warning systems are not used with implantable pacemakers for at least two reasons. First, implantable pacemakers are implanted within the body and, as such, any warning means are neither visible nor readily heard. Second, implantable pacemakers must be compact and use little power. Generally, the warning message is generated by a speaker or light source and thus draws a significant current. It is thus apparent that what is needed is an implantable cardiac event detection system that is not limited to operating on a small sample of the cardiac signal over a limited period of time, and that does not require the use of inconvenient and impractical storage devices such as tape recording systems.

Some systems have been developed that store only anomalous portions of the electrogram signal. See, e.g., Grosskopf. However, even these systems have a limited capacity and when a sufficient number of anomalous portions are stored, some data loss occurs. This data loss occurs when the memory is full and either the new signal must be discarded or the previously stored signal must be discarded. Problematically, the portion of the electrogram signal that is discarded may be the portion of signal that is needed for an accurate evaluation of the patient's heart condition. Thus, what is needed is an implantable cardiac event detection system that is not limited by the use of a finite capacity memory for storing the electrogram signal, but that provides information sufficient for programmed evaluation in a microcontroller and, if needed, automatic adjustment of a pacemaker or activation of a defibrillator in response to such evaluation.

Another problem faced by the designers of automated cardiac pacing and/or defibrillation systems is the need for analysis of the electrogram signal. One approach to accurately analyzing the electrogram signal requires that the stored electrogram signal be subjected to complex digital filtering algorithms and statistical analysis. See e.g., U.S. Pat. No. 4,422,459 issued to Simson. In order to generate the digitally filtered and statistically analyzed signals in Simson, a large computer system is employed. Such computer system is immobile and inconveniently located at, e.g., the physician's office, thus making implantation impossible. Disadvantageously, such algorithms and analysis require that many hundreds of mathematical operations be performed before an accurate conclusion as to whether the cardiac pacer and/or defibrillator are performing optimally can be obtained and, thus, before needed adjustment of the therapies provided by the cardiac pacer and/or defibrillator can be made. Problematically, this requires not only the use of a memory to store the incoming electrogram signal while the mathematical operations are being completed, the disadvantages of which are discussed above, but requires that many complicated computational steps be traversed by the microcontroller. Such complicated computational steps are highly power-consuming—which would require more frequent replacement of the battery that powers the implantable cardiac pacer and/or defibrillator—and thus, disadvantageous in implantable cardiac pacing applications.

Another approach to accurately analyzing the electrogram signal has been to allow the physician to analyze the electrogram signal stored in a memory using conventional electrogram analysis techniques. Disadvantageously, in order to obtain the stored electrogram signal, the physician must download the stored electrogram signal via a telemetry circuit in the cardiac pacer system and/or defibrillator system. Hence, because a memory is used, the problems discussed above are also present in this approach. A further disadvantage of this approach is that no automated adjustment of the therapies provided by the cardiac pacer and/or defibrillator can be made because such adjustment must wait until the patient has traveled to the physician's office and until the physician has completed his or her analysis. Thus, what is needed is an implantable cardiac data acquisition and analysis system that does not require the use of complicated and highly power-consuming mathematical computations.

SUMMARY OF THE INVENTION

The present invention advantageously addresses the above and other needs by providing an improved implantable cardiac event detection system and method usable with implantable cardiac pacemakers, cardioverters, defibrillators, or the like.

One aspect of the present invention provides an implantable cardiac event detection system which can eliminate the sensing of T-waves, reliably and dynamically set the detection threshold, and optimize the dynamic range of the incoming cardiac signal (through automatic gain control of a pre-amplifier stage) for the purpose of automatically adapting to changing cardiac signal morphology.

The system is coupled to the heart via an electrogram lead as is known in the art of cardiac pacing. The system is also coupled to a therapy circuit that provides pacing and/or defibrillation therapies to the heart. An electrogram signal is sensed through the electrogram lead and is transmitted to signal conditioning circuitry. The signal conditioning circuitry includes a pre-amplifier having a plurality of programmable gains, a narrow band filter, and digitizing circuitry. The resultant digitized electrogram signal is then coupled to a threshold detector and to a morphology detector, which are, in turn, coupled to a microcontroller. The microcontroller controls the threshold value used by the threshold detector, as well as controlling the gain of the pre-amplifier, as a function of the various morphology parameters (e.g., the previous average peak R-wave value) sensed by the morphology detector.

The threshold detector detects a cardiac event (e.g., an R-wave) within the electrogram signal whenever the electrogram signal exceeds a prescribed initial threshold value. In the preferred embodiment, the threshold detector is a digital threshold detector capable of digitally adjusting the threshold value in a predetermined stepwise fashion. The threshold detector eliminates the detection of high amplitude T-waves by increasing the initial threshold value to a temporary threshold value for a prescribed, or programmable, period of time following the detection of an R-wave. The threshold value is then gradually ramped down, in a stepwise fashion, to its initial value within a second prescribed period of time. Advantageously, the second prescribed time period may be automatically adjusted as a function of heart rate (e.g., a fast heart rate would require a fast ramp down to the initial value). In this manner, the detection of T-waves are eliminated. Thus, "double sensing" of the T-wave and false indications that a tachycardia is present cannot occur.

In the preferred embodiment, the initial threshold value is automatically determined by the microcontroller to be a percentage of the average peak (or maximum) R-wave signals over at least a period of a few minutes (e.g., at 25% of the previous peak values). Preferably, the temporary threshold value is also automatically set to a percentage of the average peak (or maximum) R-wave signals over at least a period of a few minutes (e.g., at 100% of the previous average peak values). Alternately, the initial and the temporary values could be a programmable value.

In the preferred embodiment, the gain of the pre-amplifier is automatically adjusted for the optimum dynamic range so that the incoming cardiac signal is not clipped. The control of the pre-amplifier is determined by the microcontroller and the morphology detector, as described in more detail below.

Another aspect of the present invention provides an implantable cardiac arrhythmia detection system for detecting the transition between rhythmic and arrhythmic cardiac activity in a heart using the morphology detector. One feature of the present invention is the detection of a shift in the average baseline of the rectified cardiac signal. For example, during normal sinus rhythm, the average baseline of the cardiac electrogram is approximately zero. When an arrhythmia occurs (such as, a tachycardia or fibrillation), the average baseline of the cardiac electrogram increases in magnitude. It is this detection of the shifting of the average baseline which is used, in the present invention, to detect a change in the patient's cardiac rhythm.

In one embodiment the "average baseline" may be thought of as an RMS value of the electrogram signal, or the average of the rectified signal, in that, only the positive values are considered. In the preferred embodiment, the "average baseline" is the sum of the unsigned magnitudes of a plurality of digitized samples during a prescribed interval.

Another feature of the present invention is the detection of a change in the morphology of the R-wave as a way to indicate a change between rhythmic and arrhythmic cardiac activity. For example, if the amplitude of the R-wave increase or decreases by a prescribed amount, or changes polarity, chances are that a new ectopic foci is generating R-waves from a new location, thereby indicating a change in the patient's cardiac rhythm. Furthermore, when using morphology changes in combination with the shifting of the average baseline, an even higher confidence level is achieved that the patient's cardiac rhythm has become arrhythmic.

Thus, in the present invention, the morphology detector detects various parameters associated with the morphology of the electrogram signal, and couples such parameters to the microcontroller. (Note, as used herein the term "morphology" relates to the shape of the electrogram signal when viewed as a signal waveform as a function of time.) The microcontroller then indicates the presence of an arrhythmic cardiac condition in response to a prescribed change in the morphology parameters. Such indication may then be used by the desired therapy circuit, e.g., a pacemaker, cardioverter or defibrillator, in order to deliver an appropriate therapy to the heart.

The morphology detector, according to the present invention, includes one or more of the following: a minimum detector, a maximum detector, a peak detector, a baseline averager, a baseline sampler, an accumulator, and/or an interval counter; the output signals of each being coupled to the microcontroller for determining the presence of an arrhythmia as described in more detail below.

The minimum detector, used in the morphology detector, generates a minimum signal, indicative of the magnitude of the most negative value (i.e., below a baseline voltage) in the electrogram signal and records the magnitude of such value as a minimum value.

The maximum detector generates a maximum signal, indicative of the magnitude of the most positive value (i.e., above the baseline voltage) in the electrogram signal and records the magnitude of such value as a maximum value.

The peak detector, used in the morphology detector, generates a peak signal, indicative of the largest value in the electrogram signal, regardless of whether the largest value is negative or positive.

Alternatively, the peak signal may be generated by the microcontroller, in which the microcontroller determines the peak signal to be the greater of the minimum value and the maximum value. (Note that the minimum and maximum values once determined, are both considered as positive magnitudes).

The baseline averager generates an "average baseline signal", indicative of the average magnitude of the electrogram signal over a predetermined time period. The predetermined time period may be the time during which the baseline is expected to be quiescent (e.g., as determined by the counter or by the microcontroller). Alternatively, the predetermined time period may be the entire cardiac cycle. The rationale for the latter is that during normal sinus rhythm, the average baseline signal over the entire cardiac cycle approximates the true (quiescent) baseline.

As an alternative to the baseline averager, in accordance with one embodiment of the invention, a baseline sampler may be used by the morphology detector. The baseline sampler generates an accumulated baseline signal, indicative of the accumulated magnitude (i.e., the sum of all baseline values) of the electrogram signal during the predetermined period of time. The microcontroller then counts the number of discrete sample values in the processed electrogram signal that are accumulated by the baseline sampler during the predetermined time period. In this way, a count value is generated. The total baseline value, from the baseline sampler, is then divided by such count value in order to generate the average baseline value.

Typically, the baseline sampler operates digitally. That is, the electrogram signal is sampled and digitized. The microcontroller then simply reads the magnitude of the digitized samples occurring during the predetermined time period and divides it by the total number of samples, as determined by the interval counter.

In accordance with another embodiment of the invention, the electrogram signal is not digitized (i.e. the processed electrogram signal is analog). The baseline sampler may analogically and rapidly sample the magnitudes of the processed electrogram signal over the predetermined time period. The magnitude of each of the rapid samplings (discrete values) occurring during the predetermined time period are added together. In this way, the accumulated baseline signal can be analogically generated. The accumulated baseline signal is coupled to the microcontroller, which then divides it by the time interval, as determined by, e.g., an interval counter.

The accumulator, when used within the morphology detector, generates an accumulated magnitude signal indicative of the accumulated magnitude of the electrogram signal during a cardiac cycle. The cardiac cycle begins when an R-wave is detected by the threshold detector, as described above, and ends when a subsequent R-wave is detected. The accumulator may operate digitally or analogically in the same or similar manner as the baseline sampler described above. The accumulated magnitude signal may then be divided by the total number of samples over the entire cardiac cycle to produce an average baseline signal over the entire cardiac cycle.

In one embodiment, the microcontroller provides a count signal corresponding to the number of samples in the predetermined time period (or cardiac cycle). Alternatively, the count signal is determined using a counter (as opposed to counting with the microcontroller). Such count signal is then coupled to the microcontroller, where the accumulated baseline value from the baseline sampler is divided by such count value to generate the average baseline value.

An arrhythmia flag signal is generated by the microcontroller when the quotient of the peak (or max) R-wave value divided by the average baseline value exceeds an arrhythmia threshold value (stored, e.g., in the microcontroller). The arrhythmia flag signal may then be used to engage a therapy circuit, e.g., a circuit that issues stimulation and/or defibrillation pulses in a prescribed pattern.

In addition, the microcontroller may generate one or more other morphology change signals, such as signals indicating: a change in polarity, the amplitude of the R-waves or the gain of the pre-amplifier (which is related to the envelope of the incoming cardiac signal). A control program executed by the microcontroller controls the generation of such output signals. The control program is executed in response to the detection of an R-wave, and/or a time-out signal (i.e., the time-out signal is generated in the absence of cardiac signals in order to limit the number of samples that will be acquired by the event detector).

In the discussion below, it is generally assumed that the maximum value of the cardiac signal is greater than the minimum value; however, it is to be understood that in some instances the minimum value may be larger than the maximum value. Thus, while the following discussion is directed to setting various morphology change values based on changes in the maximum value, in the event that the minimum value is greater than the maximum value, the morphology change values would instead be set in response to changes in the minimum value.

During normal sinus cardiac rhythm, the relationship between the magnitude of the maximum value and the magnitude of the minimum value does not typically change (i.e., the maximum value generally remains larger than the minimum value). In the event that the magnitude of the minimum value suddenly becomes larger than the magnitude of the maximum value, a radical change in the morphology of the electrogram signal is indicated. The microcontroller sets the morphology change value to "POLARITY" in response to such radical change. Furthermore, because it is likely that the signals thereafter generated by the morphology detector and/or the microcontroller are no longer indicative of the morphology of the previous electrogram signal, the microcontroller resets the morphology detector and/or the output signals (e.g., the minimum value, the maximum value, the peak value, and the baseline value, etc.) generated by the microcontroller in response to a change in the morphology change value, e.g., when the polarity changes.

In addition to setting the morphology change value to "POLARITY," the microcontroller may set the morphology change value to "INCREASE," "DECREASE," and/or "NONE." For example, in the event that the present maximum value (or minimum value) is much greater than the average of the preceding maximum values (or minimum values), the microcontroller sets the morphology change value to "INCREASE." When the morphology change value is set to "INCREASE," there is a high probability that a cardiac arrhythmia has begun. The therapy circuit may then respond to such detected arrhythmia as is known in the art of implantable pacemakers.

In the event that the present maximum value (or minimum value) is much lower than the average of the preceding maximum values (or minimum values), but is still greater than the minimum value (or maximum value), the microcontroller sets the morphology change value to "DECREASE." When the morphology change value is set to "DECREASE," there is a likewise high probability that a cardiac arrhythmia has begun, and the therapy circuit may thus respond accordingly.

In the event that the present maximum value (or minimum value) is not much greater or much less than the average of the preceding maximum values (or minimum values), and the present maximum value (or minimum value) remains greater than the present minimum value (or maximum value), the morphology change value is set to "NONE." This indicates to the therapy circuit that the heart is experiencing normal sinus rhythm. In this way, changes in the morphology of the electrogram signal, particularly the onset of arrhythmias, can be detected without the need for complicated and power-consuming computation by the microcontroller.

Note that in the event the peak detector is used instead of the minimum and maximum detectors, the morphology change value is set in response to changes in the peak value in a manner similar to that described above. However, it is important to note that the morphology change value is generally not set to "POLARITY" when the peak detector is used instead of the minimum and maximum detectors.

The gain change value output signal is generated by the microcontroller in response to variations in an average of the previous maximum values (or minimum values). That is, in the event that the average of the previous maximum values (or minimum values) increases substantially (e.g., as such average is updated over a period of time), the microcontroller sets the gain change value to "DECREASE" and decreases the gain of the pre-amplifier (or other sense amplifier) used as a part of the signal conditioning circuitry. Similarly, if the average of the previous maximum values (or minimum values) decreases substantially, the microcontroller sets the gain change value to "INCREASE" and increases the gain of the pre-amplifier. If the average of the previous maximum values (or minimum values) does not change substantially, the gain change value is set to "NONE" and the gain of the pre-amplifier is not changed.

The gain change value and the control of the gain of the pre-amplifier serve two functions. First, a change in the gain change value is indicative of a change in the envelope of the cardiac signal, and thus, a change in the morphology. That is, a change in gain indicates that R-waves are now being generated from a new ectopic foci. Therefore, the gain change value may be used to indicate an arrhythmia is present. Secondly, control of the gain of the amplifier helps to minimize the sensing of T-waves. That is, by maximizing the R-wave signal (by preventing clipping), the effect is to minimize the T-wave amplitude, and further enables a larger range of thresholds which can detect the R-wave without detecting the T-wave. In this way, the gain of the pre-amplifier may be adjusted in response to varying amplitudes of the electrogram signal.

In accordance with one aspect of the invention, the microcontroller sets the sensitivity of the pre-amplifier based on the gain change value. In this way, the sensitivity of the pre-amplifiers can be set to an optimum dynamic range (i.e., without clipping the cardiac signal) so that cardiac events are accurately sensed, while noise and the like are not mistaken for cardiac events.

The output signals of the microcontroller representing the average baseline value, the peak value, the arrhythmia flag value (i.e., the detected shift in the average baseline signal or the peak value divided by the average baseline), the morphology change value, and the gain change value are used to generate the average baseline signal, an average peak signal, an arrhythmia flag signal, a morphology change signal, and a gain change signal, respectively. Such output signals are coupled to the appropriate therapy circuit, and are used by the implanted therapy circuit to adjust the therapy services provided to the heart as needed.

It is thus apparent that important information is acquired from the electrogram signal without the need for external storage devices, e.g., magnetic tape recorders, and without the need for finite capacity memories. It is also thus apparent that such information is provided to the implanted therapy circuit without the need for complicated and highly power-consuming mathematical calculations in an implanted microcontroller.

In addition to the threshold detector and to the morphology detector, a time-out counter may be used with the microcontroller. During normal sinus cardiac rhythm, the time-out counter receives a reset signal when the cardiac frequency has a period shorter than a predetermined period of time. Therefore, the time-out signal is normally not generated. However, if the cardiac rhythm deviates from normal such that the cardiac frequency has a period longer than the predetermined period of time, even for one period, (such as during an episode of bradycardia, asystole, sick sinus syndrome, etc.), then the time-out signal is generated. The microcontroller then executes the control program in response to the time-out signal (e.g., to generate the peak signal, arrhythmia flag signal, morphology change signal, etc.). In this way the control program is executed when the cardiac frequency decreases below a predetermined frequency for even one period (in addition to being executed when the event sensed signal is generated as described above).

Another aspect of the time-out counter is the ability to generate a cycle length signal indicative of the period of the cardiac frequency. By dividing an accumulated magnitude value of the entire cardiac cycle by the cycle length signal, the microcontroller generates an average magnitude signal over the entire cardiac cycle.

A further aspect of the present invention provides a method of detecting the transition between rhythmic cardiac activity and arrhythmic cardiac activity. Such method includes the steps of: (a) sensing an electrogram signal; (b) determining an average baseline value; and (c) detecting a change in the average baseline value by a prescribed amount, a change less than the prescribed amount indicating rhythmic activity and a change greater than the prescribed amount indicating arrhythmic activity.

In an alternative embodiment, the method includes the steps of: (a) sensing an electrogram signal; (b) recording at least one morphology change value, (e.g., a change in polarity, a change in amplitude, a change in average baseline, or a change in gain); and (d) generating at least one output signal indicative of any change in the morphology value; which at least one output signal provides information about the electrogram signal and may be used to control a therapy circuit.

It is thus a feature of the present invention to automatically adjust the sensitivity of an implantable cardiac event detection system in response to varying electrogram signals without falsely detecting T-waves.

It is an additional feature of the present invention to easily and inexpensively acquire information from an electrogram signal over a potentially long (e.g., infinite) period of time.

It is a further feature of the present invention to acquire information from an electrogram signal without having to use external storage devices, e.g., magnetic tape recorders.

It is another feature of the invention to provide an implanted system for acquiring information from an electrogram signal without the need for large memories to store all or portions of the electrogram signal.

It is yet a further feature of the invention to provide such an implantable information acquiring system that also generates output signals that may be used by an implantable therapy circuit, such as a pacemaker, a defibrillator, or the like, and that facilitates automatic control and adjustment of the therapy provided by such therapy circuit.

It is still an additional feature of the invention to provide such a system wherein the output signals used to control the therapy circuit may be generated without the need for performing complicated and highly power-consuming mathematical computations in an implanted microcontroller.

BRIEF DESCRIPTION OF THE DRAWINGS

The above and other features of the present invention will become more apparent from the Detailed Description of the Invention, presented in conjunction with the following drawings, wherein.

Like reference numerals are used to represent like elements in the various figures and the accompanying description that follows.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
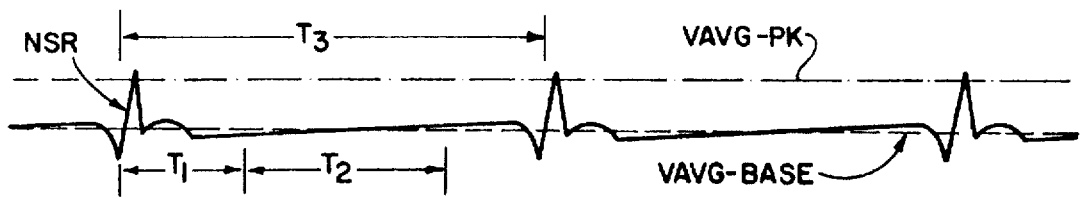
FIGS. 1, 2 and 3 show an intracardiac electrogram signal in normal sinus rhythm, tachycardia and in fibrillation, respectively, and illustrate the rational for using a shift in the average baseline to detect the transition from rhythmic cardiac activity to arrhythmic cardiac activity.
Figure 2:
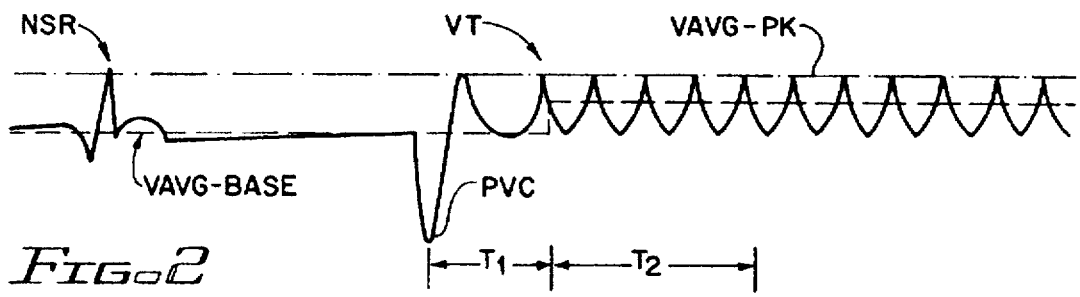
Figure 3:
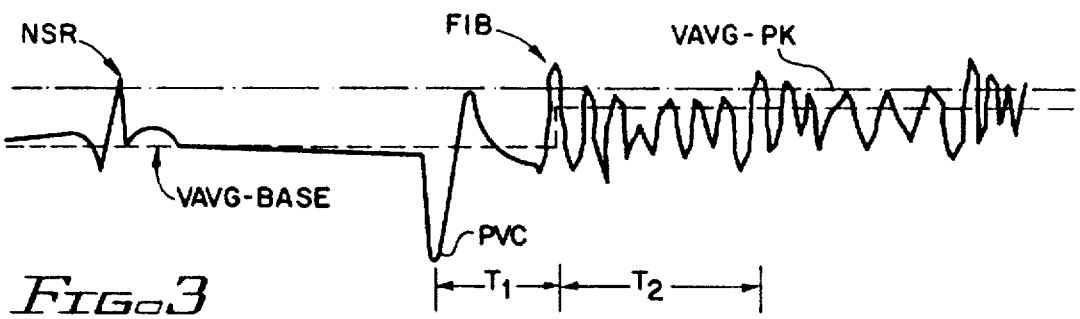

The basic premise for one aspect of the arrhythmia detection invention of the present invention is illustrated in FIGS. 1–3. FIG. 1 illustrates a cardiac electrogram which is in normal sinus rhythm (NSR). FIG. 2 illustrates a cardiac electrogram which, following a premature ventricular contraction (PVC), changes from normal sinus rhythm to ventricular tachycardia (VT). FIG. 3 illustrates a cardiac electrogram which, following a premature ventricular contraction (PVC), changes from normal sinus rhythm to ventricular fibrillation.

The present invention detects the transition from rhythmic activity to arrhythmic activity by detecting a change in the baseline average. In one embodiment, the baseline average is determined during a quiescent period of the signal, for example, during the time interval $T_2$, following a delay time interval, $T_1$, as shown in FIGS. 1, 2 and 3. The delay period, $T_1$, is chosen to begin after the repolarization signal (T-wave) has ended. In another embodiment, the baseline average is determined over the entire cardiac cycle (i.e., during the time interval $T_3$), since this average closely approximates the true, or quiescent, baseline.

In the simplest embodiment, an increase in the average baseline beyond a predetermined threshold voltage will indicate a change in morphology, such as ventricular tachycardia and ventricular fibrillation, as shown in FIGS. 2 and 3, respectively. The predetermined threshold voltage would be characterized at implant for a given patient.

In the preferred embodiment, to determine the shift in the baseline, the average peak (or max) R-wave value is divided by the average baseline and then compared to an arrhythmia threshold. If the result is greater than an arrhythmia threshold (also characterized at implantation), an arrhythmia flag signal is generated. For example, in FIG. 2 (or FIG. 3), after the delay period, T1, the system will begin to sample the baseline average during the time interval T2. At the end of T2, a higher baseline value is found as a result of the ventricular tachycardia (or ventricular fibrillation). This higher baseline value is sent to a microcontroller, which in turn, computes the quotient of the average peak R-wave value with the new baseline average. If the result is greater than the patient's arrhythmia threshold, then the system indicates that there is a high probability that an arrhythmia has begun. Furthermore, it may be possible to use the quotient of the average peak divided by the baseline to discriminate between VT and VF.

Since the arrhythmia detection system of the present invention is based on accurately detecting the peak amplitude of an R-wave, it can be appreciated by one skilled in the art that it is critical that T-waves are not detected. Thus, an implantable cardiac event detection that eliminates T-waves is also described below.

Figure 4:
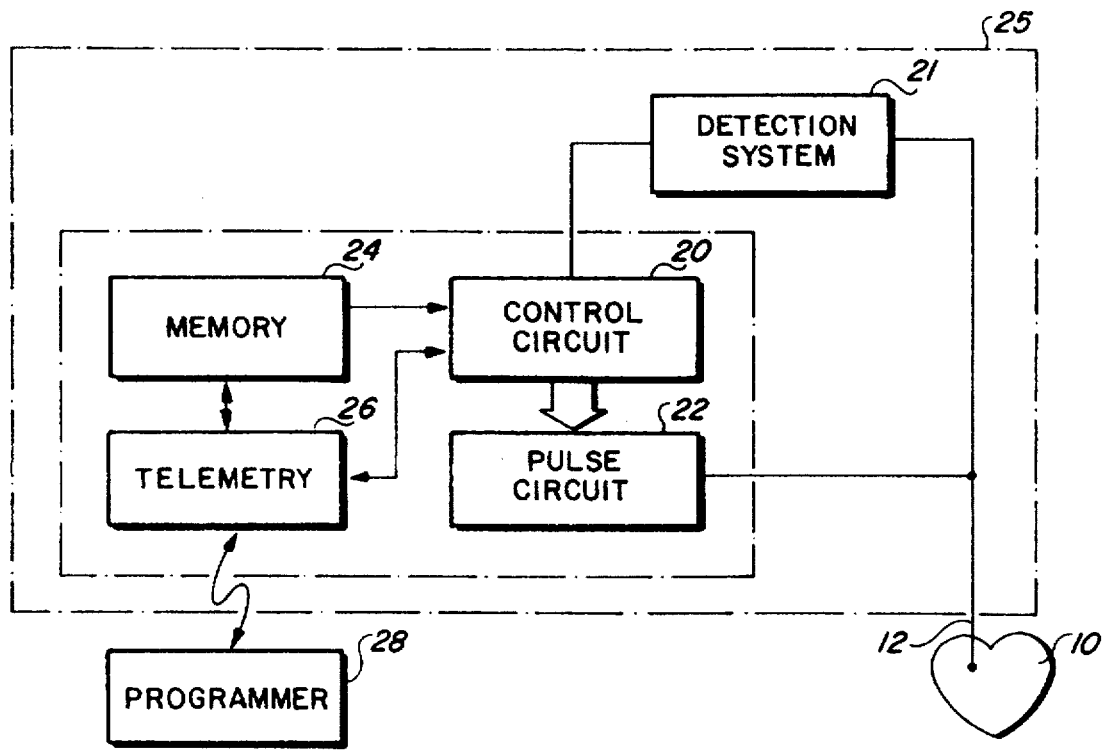
FIG. 4 is a block diagram showing a cardiac event and arrhythmia detector of the present invention in conjunction with an electronic therapy circuit.

In FIG. 4, a block diagram is shown of a cardiac detection system 21 used with an electronic therapy circuit 23. The cardiac detection system 21 and the therapy circuit 23 comprise, in combination, an implantable device 25 that is implanted into a patient and attached to a heart 10 of the patient via an electrogram lead 12. The electrogram lead provides electrical communication between the implantable device 25 and the heart 10. One signal that is communicated through the electrogram lead 12 from the heart 10 to the implantable device 25 is an electrogram signal. Such electrogram signals (sometimes referred to as EGM signals) are known in the art. See, e.g., U.S. Pat. Nos. 4,596,255; 4,712,555; 4,817,605; and 4,940,052; incorporated herein by reference. The electrogram signal is coupled, within the implantable device 25, to the cardiac detection system 21. The implantable device 25 is housed in an implantable, hermetically sealed housing as is known in the art of implantable electronic pacemakers.

The cardiac detection system 21 processes the electrogram signal and generates at least one output signal. The output signal is coupled to the therapy circuit 23, which therapy circuit may be considered as a cardiac pacing system (e.g., an implantable pacemaker, a cardioverter or a defibrillator). The therapy circuit 23 controls the therapy delivered to the heart 10 (typically stimulation pulses) via the electrogram lead 12. Alternatively, another lead (e.g., a pacing lead) may be used in lieu of or in addition to the lead 12 in order to deliver the desired therapy (e.g., stimulation pulses) to the patient's heart.

By way of example, in FIG. 4, the therapy circuit 23 comprises a cardiac pacer. The therapy circuit 23 includes a control circuit 20, pulse generator circuitry 22, a memory circuit 24, and a telemetry circuit 26. In practice, the control circuit 20 (which may hereafter be referred to simply as a "microcontroller") and the memory circuit 24 (hereafter referred to as a "memory") may advantageously be utilized by both the cardiac detection system 21 and the therapy circuit 23, thereby assuming both therapy-providing and event-detecting functions. However, to more clearly illustrate the present invention, the control circuit 20 and the memory circuit 24 are shown as separate elements of the therapy circuit 23, even though shared by the cardiac detection system 21. In some embodiments, the cardiac detection system 21 may utilize a separate microcontroller from the control circuit 20 and memory circuit 24 of the therapy circuit 23.

The control circuit 20 receives the output signal from the cardiac detection system 21 and, in response thereto, evaluates whether or not optimum therapy is being delivered to the heart 10. If the therapy being delivered is not optimum, the control circuit 20 makes adjustments, as required. In response to the adjustment of the therapy, the pulse generator circuitry 22 begins delivering a more optimum therapy to the heart 10. Several adjustments of the pulse generator circuit 22 may be needed before an optimum therapy is delivered. Under some circumstances, less than optimum therapy may be the best therapy that can be delivered. This is because the output signal may rapidly change in response to changing conditions of the heart 10 before needed adjustments can be made in response to previous output signals. However, the therapy delivered to the heart 10 will, in general, be repeatedly adjusted until optimum or near optimum therapy is delivered to the heart 10.

In determining what is optimum therapy, based on the output signal generated by the cardiac detection system 21, the control circuit 20 may also use a memory circuit 24. Various control parameters are stored in the memory circuit 24 by a physician using a telemetry circuit 26. In order to store such parameters, the physician utilizes an external (non-implanted) programmer 28 that is coupled to the memory circuit 24 and/or the control circuit 20 via the telemetry circuit 26 and a suitable communication link 27. Telemetry circuits used for this purpose are known in the art.

Alternatively, various other therapy circuits 23 may be utilized with the cardiac detection system 21 of the present invention, such as other types of cardiac pacers or stimulators, implantable electrical defibrillators, implantable monitoring devices, and the like.

Figure 5:
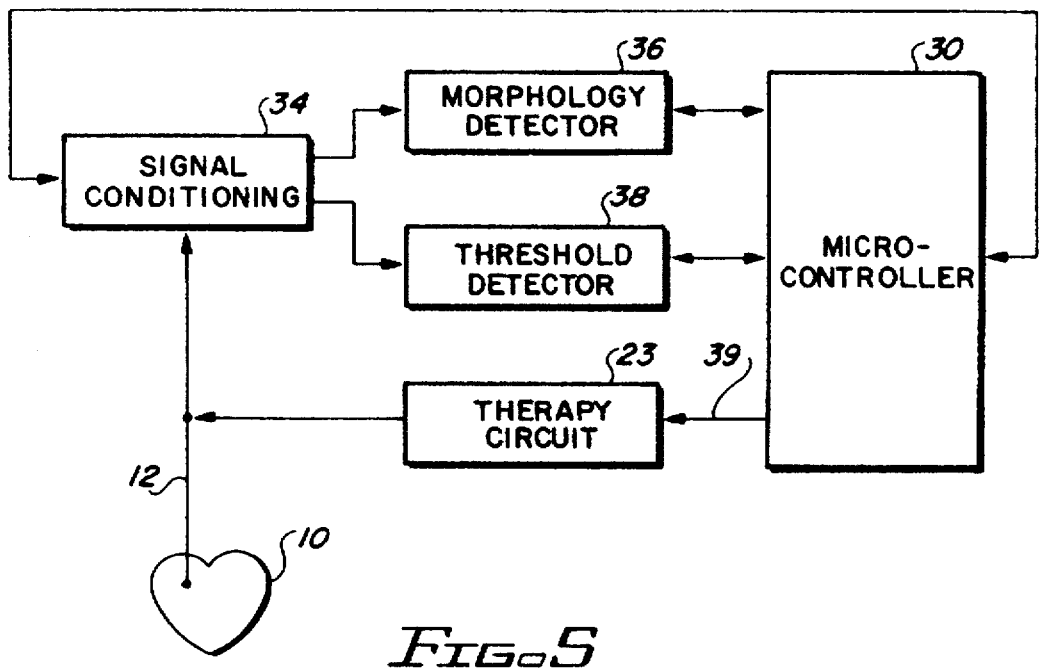
FIG. 5 is a basic block diagram of one embodiment of a cardiac event and arrhythmia detector made in accordance with the present invention.

In FIG. 5, a basic block diagram of the cardiac detection system 21 is shown. As seen in FIG. 5, the heart 10 and electrogram lead 12 are coupled to signal conditioning circuitry 34. The signal conditioning circuitry 34, in turn, is coupled to a morphology detector 36 and a threshold detector 38. The two detectors 36 and 38 are coupled to a microcontroller 30. The microcontroller 30 is further coupled to the signal conditioning circuitry 34 and to the therapy circuit 23.

The electrogram signal is transmitted to the signal conditioning circuitry 34 via the electrogram lead 12 and is processed by the signal conditioning circuitry 34 into a plurality of discrete values. The discrete values are transmitted to the threshold detector 38 and to the morphology detector 36. The threshold detector 38 compares the amplitude of each of the discrete values with an threshold value that is set by the microcontroller 30. In the event that the amplitude of one of the discrete values exceeds the event threshold value, an event sensed signal is generated by the threshold detector 38. The event sensed signal is then coupled to the microcontroller 30.

Simultaneously, the morphology detector 36 evaluates each of the discrete values to determine the morphology of the electrogram signal. In response to this evaluation, the morphology detector 36 generates at least one morphology value that is coupled to the microcontroller 30. The morphology value is used by the microcontroller 30 to adjust the sensitivity of the signal conditioning circuitry 34, e.g., either by adjusting the gain of an amplifier, the threshold or by adjusting the narrow band filter bandwidth. Additionally, the morphology value is used by the microcontroller 30 to generate an output signal. The output signal is coupled to the therapy circuit 23 over signal line 39. Such output signal adjusts the therapy circuit 23 to deliver a more optimum therapy to the heart 10 via the electrogram lead 12.

Figure 6:
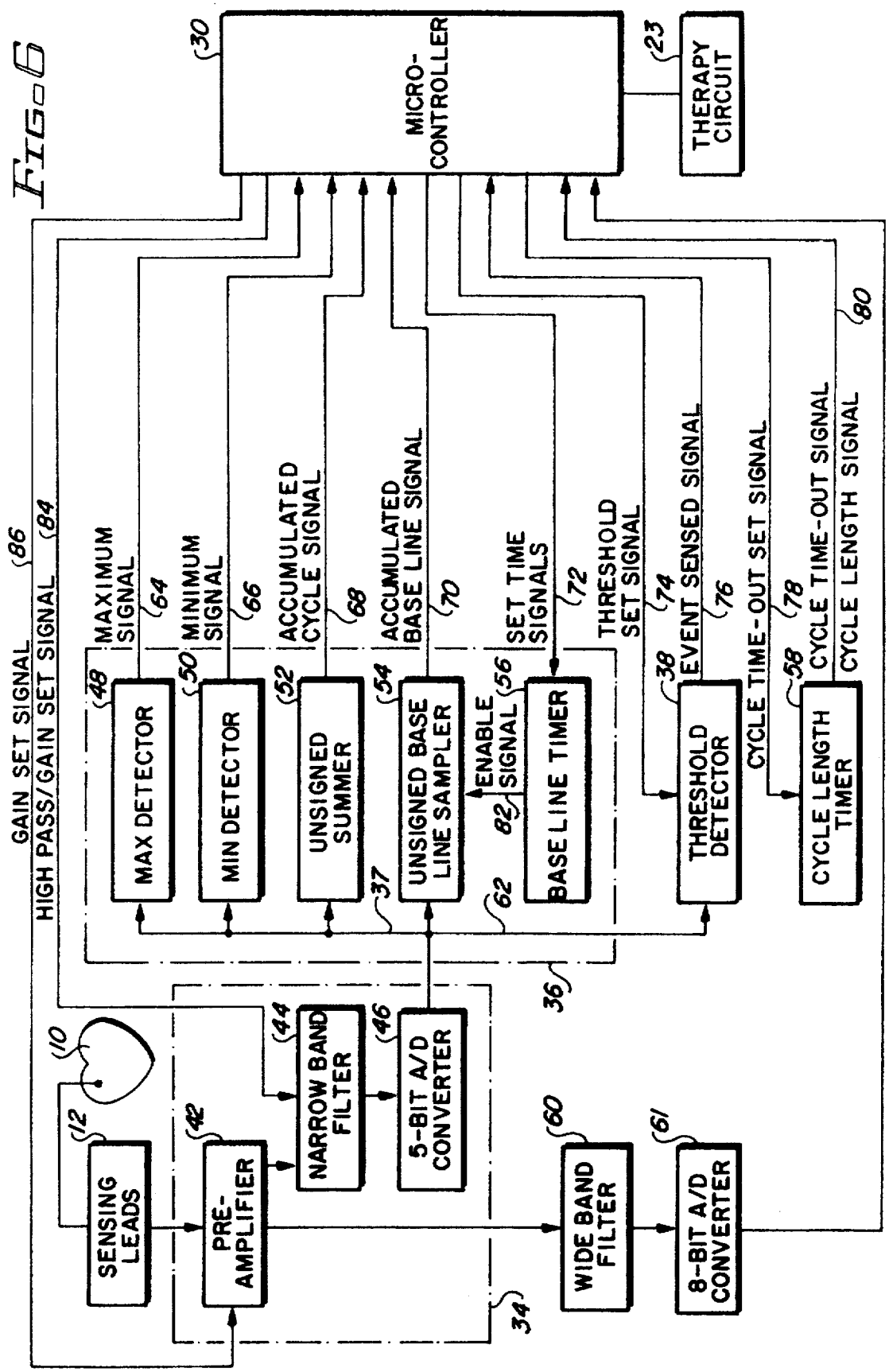
FIG. 6 is a detailed block diagram of the cardiac event detector shown in FIG. 5.

In FIG. 6, a detailed block diagram of the cardiac detection system 21 is shown. The signal conditioning circuitry 34, threshold detector 38, morphology detector 36, microcontroller 30 and therapy circuit 23 are shown. The signal conditioning circuitry 34 is comprised of a pre-amplifier 42 that is coupled to the electrogram lead 12; a narrow band filter 44 that is coupled to the pre-amplifier 42; and a 5-bit A/D converter 46, coupled to the output of the narrow band filter 44, which converts the filtered signal to a digital signal. The output of the A/D converter 46 is directed to the morphology detector 36 and the threshold detector 38.

In addition, a wide band filter 60 and an 8-bit analog-to-digital (A/D) converter 61 are shown coupled between the signal conditioning circuitry 34 and the microcontroller 30. Such wide band filter 60 and A/D converter 61 advantageously provide a signal path through which the microcontroller 30 may directly monitor a digitized version of the electrogram signal in addition to the processing of the electrogram signal by the threshold detector 38 and the morphology detector 36.

The pre-amplifier 42 amplifies the electrogram signal from the electrogram lead 12 using a gain amplitude that is controlled by a 3-bit gain set signal from the microcontroller 30. The gain set signal is generated in response to a control program discussed more completely below in reference to FIGS. 9–13.

Included in the electrogram signal are various noise signals, e.g., undesirable components such as a T-wave, electromagnetic interference, myopotential voltage signals, and "baseline wander." (Baseline wander is a deviation, or drift, of the voltage of the electrogram signal during what should be the electrically quiet part of the electrogram signal.) Each of these noise components have been recognized in the art. After the electrogram signal is amplified, it is coupled to the narrow band filter 44. The narrow band filter 44 filters out most of the undesirable noise components in the amplified electrogram signal, and removes the need to compensate such signal for baseline wander in the control program.

Sometimes it is desirable to widen or narrow the pass band of the narrow band filter 44, e.g., to adapt to different slew rates in the electrogram signal that occur at the onset of an arrhythmia, as well as to compensate for variations due to different electrogram lead types and positions. Advantageously, the pass bandwidth of the narrow band filter 44 can be adjusted in response to a high pass set signal obtained from the microcontroller 30. The high pass set signal is generated by the control program, or alternatively may be programmed to a desired value via the telemetry circuits and external programmer described above. It is known that arrhythmia signals have lower frequency content, so when the signal is not a positively stable normal sinus rhythm, the bandwidth of the filter is widened.

The output of the narrow band filter 44 is coupled to the 5-bit A/D converter 46. In one embodiment, the 5-bit A/D converter 46 transforms the amplified, filtered electrogram signal into one of thirty-two possible 5-bit digital codes. The conversion rate of the converter is about 1000 Hz, and the converter has two interleaved phases. During the first phase, a positive input produces a non-zero code (discrete value) indicative of the magnitude of the input, and a negative input produces a zero output. During the second phase, a positive input produces a zero output, and a negative input produces a non-zero output code (discrete value) indicative of the magnitude of the input. The 5-bit A/D converter 46 traverses one of these two phases during each conversion, and alternates between the first phase and the second phase during succeeding conversions.

The 5-bit converter 46 also provides a polarity signal indicating the polarity of the last discrete value output therefrom, and an end-of-conversion signal indicating that an output code has been latched onto a 5-bit output bus of the A/D converter 46. The 5-bit output bus, polarity signal and the end-of-conversion signal are coupled to the threshold detector 38 and the morphology detector 36 over signal bus 37.

As seen in FIG. 6, the threshold detector 38 generates an event sensed signal when an output from the 5-bit A/D converter 46 is larger than a threshold value. Note that this is an unsigned comparison: a discrete value of either polarity (negative or positive) that exceeds the threshold will cause the event sensed signal to be generated by the threshold detector 38. The microcontroller 30 sets a starting threshold value after the detection of a cardiac event, e.g., an R-wave. This starting threshold value is a function of the previous detected peak and average values of the R-wave as described more fully below in conjunction with FIGS. 10 and 11. Additionally, the microcontroller 30 prevents discrete values from being received by the threshold detector 38 until a programmable (e.g., 0 to 50 ms) refractory time period has elapsed after the deliverance of the therapy to the heart 10 by the therapy circuit 23. Such action prevents spurious re-detections of, e.g., a R-wave, after the therapy has been delivered to the heart 10.

One of the problems frequently encountered with some patients is a large T-wave, representing the repolarization of the cardiac tissue. The T-wave follows the depolarization of cardiac tissue, i.e., the R-wave. It is extremely important in a cardiac arrhythmia detection system that the T-wave not be confused with the R-wave. However, in patients exhibiting a large T-wave, the T-wave may be of the same order of magnitude as the R-wave. Hence, the detection circuitry, if detection is based solely on the electrogram signal exceeding a prescribed threshold value, has no way to distinguish T-waves from R-waves.

The present invention advantageously addresses this problem by providing a threshold value to the threshold detector 38 that automatically adjusts the threshold value to a low value (increased sensitivity) in order to best detect the R-wave, and (after the R-wave has been detected) to a high value (decreased sensitivity) in order to best avoid detection of the T-wave. After a sufficient time period at the decreased sensitivity, selected to avoid detection of the T-wave, the threshold value is then gradually decreased to its prior low value (i.e., the sensitivity is gradually increased) in anticipation of detecting the next R-wave.

Figure 7:
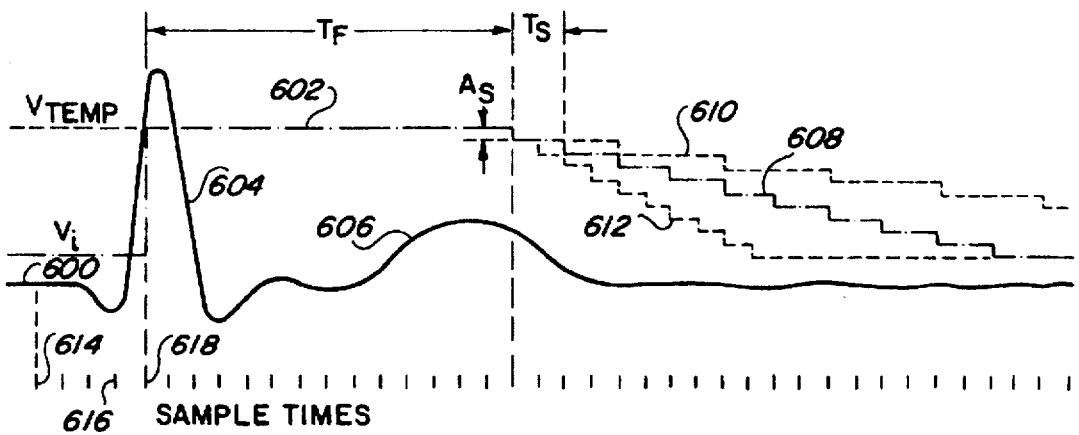
FIG. 7 is a graph showing an exemplary electrogram signal used as an input to the pre-amplifier of FIG. 6, and a representation of the dynamic threshold adjustment by the microcontroller.

The manner of automatically adjusting the threshold value of the threshold detector 38 in accordance with the present invention is graphically depicted in FIG. 7. Represented in FIG. 7 are both an electrogram signal 600, containing an R-wave 604 and a T-wave 606, and a dynamic threshold value 602. Also included in FIG. 7 are "sample times," represented as tick marks along the horizontal axis. As described previously, the electrogram signal 600 is sampled each sample time by the A/D converter 46 (FIG. 6), with the resulting sampled value being examined by the threshold detector 38. If at any given sample time the value of the electrogram signal 600 is less than the dynamic threshold value 602, then no cardiac event detection occurs. If, however, at a given sample time the value of the electrogram signal 600 is greater than the dynamic threshold value 602, then a cardiac event detection occurs.

Thus, as shown in FIG. 7, at sample time 614, before the occurrence of the R-wave 604, the dynamic threshold value 602 is set to a low initial value (indicated as $V_i$) in anticipation of detecting an R-wave. At sample time 614, the electrogram signal 600 is less than the dynamic threshold value 602 so no R-wave detection has yet occurred. Between sample times 616 and 618, the R-wave 604 begins, causing the electrogram signal 600 to cross over the dynamic threshold value 602, thereby signaling the occurrence of the R-wave. As soon as the R-wave is detected in this manner (i.e., at the next sample time 618 following the detection of the R-wave), the dynamic threshold value 602 increases to its predetermined temporary value (indicated as $V_{temp}$). Such predetermined temporary threshold value is determined as a function of the detected average values (e.g., average peak, average max, etc.) of prior cardiac events, as explained more fully below in conjunction with FIGS. 10 and 11. Alternatively, in some embodiments of the invention, the temporary threshold value and/or the initial threshold value may be a programmed value, selected by the physician at the time of implant or thereafter.

Once the dynamic threshold value 602 has been increased to the predetermined temporary value, the dynamic threshold value 602 remains fixed at such value for a predetermined, or programmable, period of time, $T_F$. Typically, $T_F$ is defined to be a programmable number of sample times of the A/D converter 46, e.g., 10 to 15 sample times (which corresponds to 10 to 15 ms, assuming a sample rate of 1000 Hz). The time, $T_F$, during which the dynamic threshold value 602 remains fixed at the temporary threshold value is selected to be sufficiently long to pass over a typical T-wave for the particular patient whose electrogram is being monitored.

At the conclusion of the time, $T_F$, the dynamic threshold value 602 ramps down, in a controlled manner, from the temporary value, $V_{temp}$, to the initial value, $V_i$. In a preferred embodiment, such ramping down occurs by defining the dynamic threshold value 602 to be a number of between 0 and 31, with 0 indicating the lowest (most sensitive) threshold value, and with 31 indicating the highest (least sensitive) threshold value. As the threshold value ramps down from its temporary value to its initial value after the time period $T_F$, it does so by decrementing the dynamic threshold value 602 by one for a prescribed number of sample periods. For example, as shown by the ramp down curve 608 in FIG. 8, the dynamic threshold value is decremented by one for each two sample times, until the dynamic threshold value reaches the initial value.

In some instances, it is desirable to adjust the ramp down rate of the dynamic threshold value 602. For example, while the ramp down curve 608 in FIG. 7 may be adequate for a given patient while at rest (having, e.g., a heart rate of 60 beats per minute, or one beat per second), it may be totally inadequate if the patient's heart rate suddenly increases because it may not be fully ramped down before the next R-wave occurs. Thus, the present invention includes a feature for automatically adjusting the ramp down rate as a function of the sensed heart rate. If the sensed heart rate is slow, then a relatively slow ramp down rate can be used, such as is represented by the ramp down curve 610 in FIG. 7 (decrementing one unit for each four sample times). If the sensed heart rate is moderate, then a moderate ramp down rate can be used, such as the ramp down curve 608 in FIG. 7 (decrementing one unit for each two sample times). If the sensed heart rate is fast, then a fast ramp down rate can be used, such as the ramp down curve 612 in FIG. 7 (decrementing one unit for each sample time).

Advantageously, the adjustments of the threshold value, including the ramp down rate, may occur under control of the microcontroller 30 (FIG. 6) by simply providing the threshold detector 38 with a threshold set signal. The threshold set signal includes, in a preferred embodiment, at least three separate elements: a threshold set value; a threshold decrement interval value; and a detect refractory set value. The threshold set value may comprise, e.g., 5 bits (corresponding to 32 values). The threshold decrement interval value may comprise, e.g., 2 bits (corresponding to four values). Such decrement interval value effectively sets the ramp down rate, as described above, thereby providing four different ramp down rates. The detect refractory set value may comprise, e.g., 4 bits (corresponding to 16 values). The detect refractory set value effectively sets the duration of the time $T_F$ during which the threshold value remains fixed at the temporary value. It is to be emphasized, of course, that the above values are only exemplary, and that any number of bits may be used to define the indicated variables in order to suit the needs of a particular application of the invention.

As evident to those of skill in the art, the actual implementation of the threshold detector 38 may occur in software (i.e., within the microcontroller 30 and/or in hardware using, for example, appropriate registers and logic gates). Such registers and logic gates may be configured in conventional manner to digitally compare two digital numbers, one of which is the sample value and the other of which is the threshold value, and to decrement the threshold value as defined by the detect refractory set value (fixed threshold time, $T_F$) and the threshold decrement interval value (ramp down rate).

With reference to FIG. 6, it is seen that the morphology detector 36 is comprised of a plurality of detectors: a maximum detector 48, a minimum detector 50, an accumulator (or summer) 52, a baseline sampler 54, and a counter (or baseline timer) 56. Each of these detectors is coupled to the output bus 37 connected to the A/D converter 46.

The maximum detector 48 latches the value on the output bus 37 if: (1) its magnitude exceeds the value currently stored by the maximum detector 48 (initially zero), and (2) the polarity output is positive, thereby always trapping the most positive discrete value. The minimum detector 50 latches the value on the output bus 37 if: (1) its magnitude exceeds the value currently stored by the minimum detector 50 (initially zero), and (2) the polarity output is negative, thereby always trapping the most negative discrete value. Thus, together the maximum and minimum detectors 48 and 50 completely bracket the excursion of the digitized electrogram signal. The maximum and minimum detectors 48 and 50 reset themselves (i.e., reset the value currently stored in the detectors 48 and 50 to zero) each time the microcontroller 30 reads them. This is normally at the end of a cardiac cycle.

The accumulator 52 (labeled in FIG. 6 as an "unsigned summer") sums, or totals, all of the discrete values produced by the A/D converter 46 during the current cardiac cycle (i.e., since the previous event sensed signal was generated by the threshold detector 38 without regard to polarity). Each time the A/D converter 46 issues an end-of-conversion signal, the conversion (discrete value) is latched and added to a previous accumulated magnitude value in the accumulator 52, thereby forming a new accumulated magnitude value. Thus, the accumulated magnitude value is representative of the total magnitude of all of the discrete values issued by the A/D converter 46 during the current cardiac cycle.

The baseline sampler 54 (labeled in FIG. 6 as an "unsigned baseline sampler") sums, or totals, all discrete values produced by the A/D converter 46 during a predetermined time period. The purpose of the baseline sampler 54 is to sample what should be the electrically quiet (baseline) part of the electrogram signal that lies between intracardiac waveform complexes. During normal sinus cardiac rhythm, the sum collected by the baseline sampler 54 will be small and a sudden increase in the sum indicates the probability that a cardiac arrhythmia is in progress.

The baseline sampler 54 (FIG. 6) is enabled by the baseline timer 56. The baseline timer 56 provides an enable signal that enables the baseline sampler during the predetermined period of time. In one embodiment, the predetermined period of time is defined by two set time signals generated by the microcontroller 30: a set delay time signal $T_1$, and a set sample time signal, $T_2$. The set delay time signal determines a delay period after the detection of an event by the threshold detector 38 during which the enable signal is not present and, hence, during which the baseline sampler circuit is not enabled. The set sample time signal defines a sample period or sample window after the delay period during which the enable signal is present and hence during which the baseline sampler circuit 54 is monitoring the electrogram signal. After the sample period or window, the enable signal is not generated. By selecting appropriate values for the delay period, typically 100 to 150 ms, and for the sample period or window, typically 20 to 50 ms, the baseline sampler 54 is enabled during the quiet (baseline) part of the electrogram signal. In an alternative embodiment, the average baseline is computed over an entire cycle length, since such calculation closely approximates the true, or quiescent, baseline.

While the baseline sampler 54 is enabled, it sums, or totals, all discrete values produced by the A/D converter 46. Each time the 5-bit A/D converter 46 issues an end-of-conversion signal, the conversion is latched and added to the previous total baseline value in the baseline sampler 54, thereby forming a new total baseline value.

A time-out detector, referred to as a cycle length counter 58 in FIG. 6, is also coupled to the microcontroller 30. The cycle length counter 58 serves two functions. First, the cycle length counter 58 counts the number of end-of-conversion signals that are produced by the A/D converter 46 during a cardiac cycle, and thereby generates a cycle length value. (Note, each end-of-conversion signal occurs at a known rate (e.g., 1000 Hz) and thus has a known time period (e.g., 1 ms) associated therewith. Thus, the occurrence of 772 end-of-conversion signals, for example, indicates a time period of 772 ms. Each time the microcontroller 30 reads the cycle length counter 58, the cycle length counter 58 is cleared (i.e., the timer begins to count from zero). Second, the cycle length counter 58 generates a cycle time-out signal if the count exceeds a preset number. The preset number (which corresponds to a preset time period) is set by the microcontroller 30 in accordance with the control program or in accordance with a value stored in the memory circuit 24 via the telemetry circuit 26 as described above (FIG. 4). The occurrence of the cycle time-out signal forces the microcontroller 30 to read the morphology detector 36 in the event no cardiac event is sensed during the preset time period.

Figure 8:
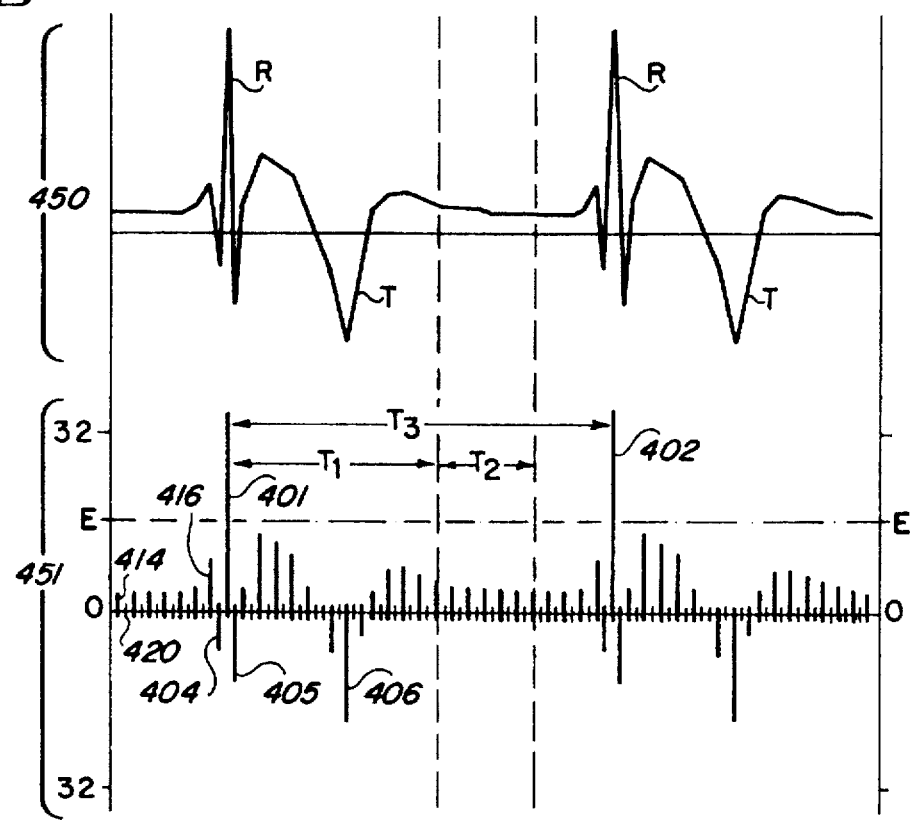
FIG. 8 is a graph showing an exemplary electrogram signal used as an input to the cardiac threshold detector of FIG. 5, and a digitized electrogram signal generated in response to the electrogram signal by a signal processor that is part of the morphology detector of FIG. 6.

In FIG. 8, an exemplary intracardiac electrogram signal 450 is shown to illustrate a typical input signal to the cardiac detection system 21 and to further graphically represent a digitized electrogram signal 451 generated in response to the electrogram signal 450 by the signal conditioning circuitry 34.

Referring first to the electrogram signal 450, it can be seen that the electrogram signal is made up of five basic wave structures. First in the electrogram signal 450 is the Q-wave, immediately followed by the R-wave, and then the S-wave. These three waves are commonly referred to as the QRS complex. The QRS complex is followed by the T-wave, and then the barely discernible P-wave. After passing through the narrow band filter 44 (FIG. 6), the T-wave and the P-wave are usually not discernible. After the P-wave, the cycle repeats beginning with the QRS complex. The period, $T_3$, of the electrogram signal, from QRS complex to QRS complex, is referred to as the cardiac cycle. The period $T_3$ for the electrogram signal 450 shown in FIG. 8 may be in the range of approximately 800 to 300 ms (corresponding to a rate of approximately 70 to 200 ppm).

The digitized electrogram signal 451, also shown in FIG. 8, reveals that the 5-bit A/D converter produces a non-zero output code 414 during a first sample period, approx. 1 ms, because the input electrogram signal 450 is positive when the electrogram signal is digitized and the A/D converter 46 is in the first phase, as mentioned above. During a second sample period, an output code 420 is produced that is zero because the input electrogram signal is still positive and the A/D converter 46 is in the second phase, as mentioned above. This process continues with every other sample period producing a non-zero output code (indicative of a positive input electrogram signal) until the occurrence of the Q-wave. With the occurrence of the Q-wave, a negative excursion of the electrogram signal first occurs, as indicated at 404. Immediately following the negative excursion 404, a positive excursion occurs at 401, representative of the positive R-wave being detected. The amplitude of the digitized electrogram signal at 401 exceeds the threshold value represented by line E—E. Exceeding the threshold E—E causes the threshold detector 38 to generate the event sensed signal described above.

When the R-wave is detected, a delay period, $T_1$, begins during which the baseline sampler 54 is disabled. Following the delay period, $T_1$, a sample period, $T_2$, begins during which the baseline sampler 54 is enabled. As explained above, the baseline sampler is disabled after the sample period, $T_2$, until the next sample period begins. The next delay period begins after the next event sensed signal is generated at 402. This will occur when the digitized electrogram signal again exceeds the threshold value designated by line E—E.

It should be noted that the sample periods shown in FIG. 8 are, for reasons of clarity, not drawn to scale relative to the horizontal (time) axis. A typical cardiac cycle, for example, may be 1000 ms (corresponding to 60 heartbeats per minute). At a sample rate of 1000 Hz, one sample would be made every 1 ms, or 1000 samples would be made during a cardiac cycle. For purposes of clarity, however, only about 48 to 50 samples are shown in FIG. 8 as being taken during the cardiac cycle, T3.

In FIGS. 9, 10, 11, 12 and 13, a flowchart of a control program used by the microcontroller 30 is shown. Each main step of the flowchart is shown as a "box" or "block," with each box or block having a reference numeral associated therewith. The control program is called by the microcontroller 30 whenever the microcontroller 30 receives the event sensed signal from the threshold detector 38 or receives the cycle time-out signal from the cycle length detector 58 (Block 1001). Under the direction of the control program, the microcontroller 30 reads the minimum value, the maximum value, the total baseline value and the cycle length value (Block 1003) of the electrogram signal during a given cardiac cycle. Note that the maximum and minimum detectors, the baseline sampler, and the cycle length detector are reset (to zero) after they are read by the microcontroller 30. The average baseline value is then calculated by dividing the total baseline value by the number of sample delay values (Block 1005). Next the average baseline value is subtracted from the maximum value (Block 1007) and from the minimum value (Block 1009), thereby removing any normally distributed noise level. A variable called current polarity is set equal to the polarity value of the discrete value that caused the event sensed signal to be asserted.

Figure 10:
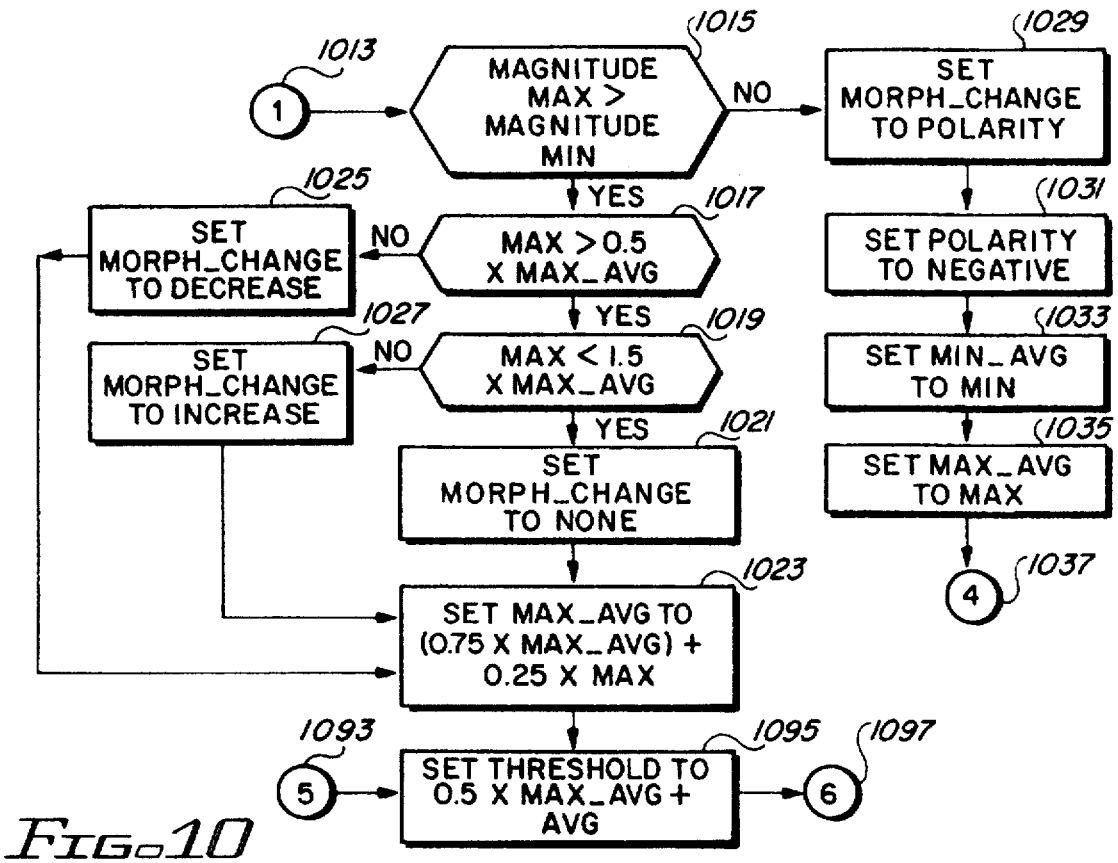
Figure 11:
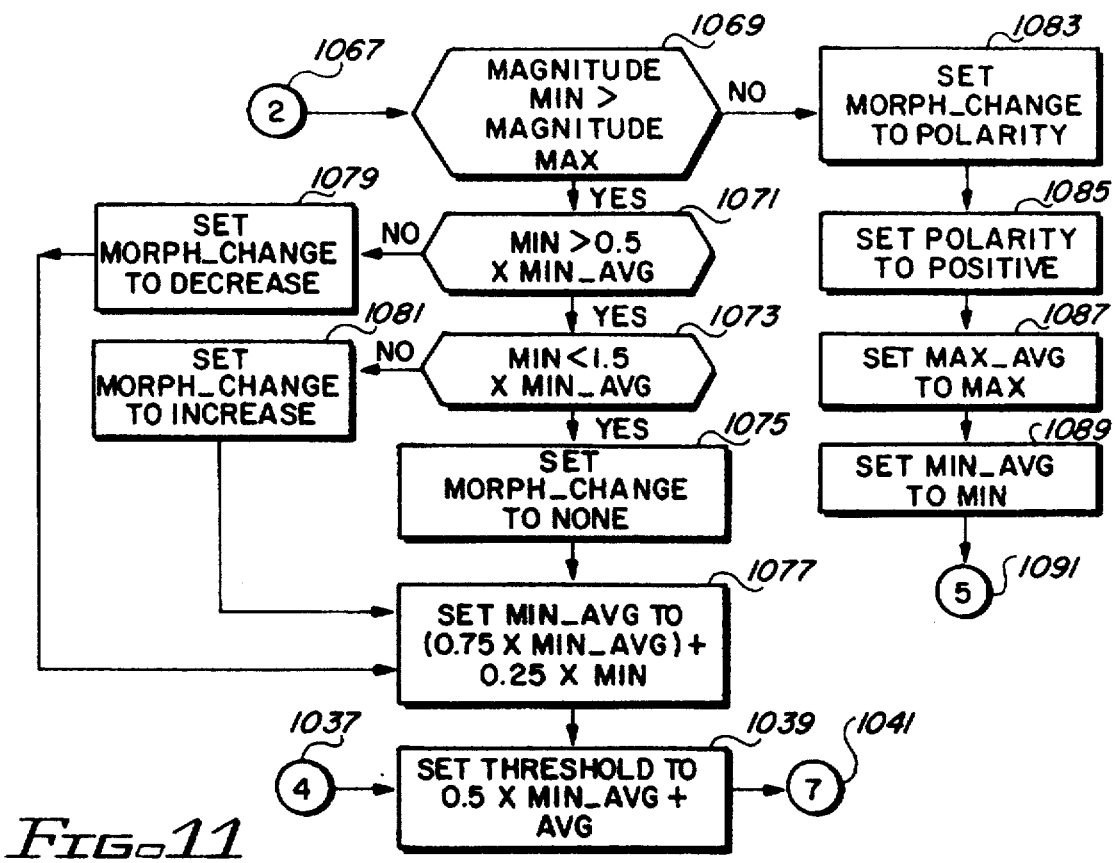

The following discussion assumes that the current polarity variable is positive, however, symmetrical operation would occur if the current polarity variable were negative. The current polarity is tested (Block 1011) and, if the polarity is positive, execution proceeds at Block 1013 (FIG. 10). The magnitude of the maximum value is compared with the minimum value (Block 1015). During normal sinus rhythm, the maximum value will be larger than the minimum value whenever the current polarity variable is positive. If the maximum value is smaller than the minimum value, a radical change in the morphology of the electrogram signal is indicated. In response to this radical change, the MORPH_CHANGE variable is set to "POLARITY" (Block 1029), the polarity variable is set to negative (Block 1031), the variable MIN_AVERAGE is set equal to the current minimum value (Block 1033) and the variable MAX_AVERAGE is set equal to the current maximum value (Block 1035). It is important that the MIN_AVERAGE and the MAX_AVERAGE variables be set to the current minimum and maximum values, respectively, because there is no reason to assume that these average variables are meaningful after such a radical change in morphology. The generation of MIN_AVERAGE and MAX_AVERAGE is discussed below. Execution of the program continues in Block 1037 (FIG. 11).

If the maximum value is larger than the minimum value (as determined at Block 1015 of FIG. 10), the maximum value is compared to the MAX_AVERAGE variable (Blocks 1017 and 1019). If the maximum value is smaller than one-half times the MAX_AVERAGE variable, the variable MORPH_CHANGE is set to "DECREASE" (Block 1025); and if the maximum value is greater than one and one-half times the MAX_AVERAGE variable, the variable MORPH_CHANGE is set to "INCREASE" (Block 1027). If the maximum value is between one-half times the MAX_AVERAGE, and one and one-half times the MAX_AVERAGE, the variable MORPH_CHANGE is set to "NONE" (Block 1021).

Next, the variable MAX_AVERAGE (Block 1023) is updated using the following relationship:

MAX_AVERAGE=¾(MAX_AVERAGE)×¼(maximum value)

The threshold value (Block 1095) is generated according to the following relationship:

THRESHOLD VALUE=½(MAX_AVERAGE)+ (average baseline value)

Figure 12:
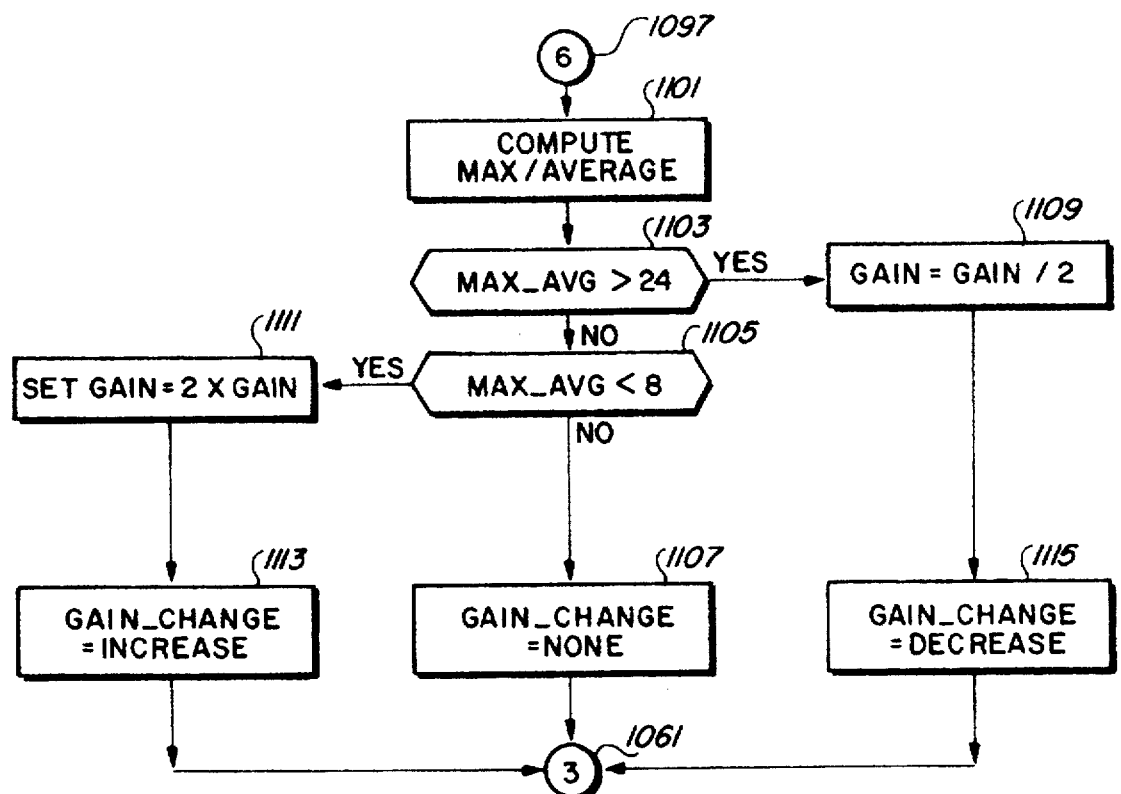
Figure 13:
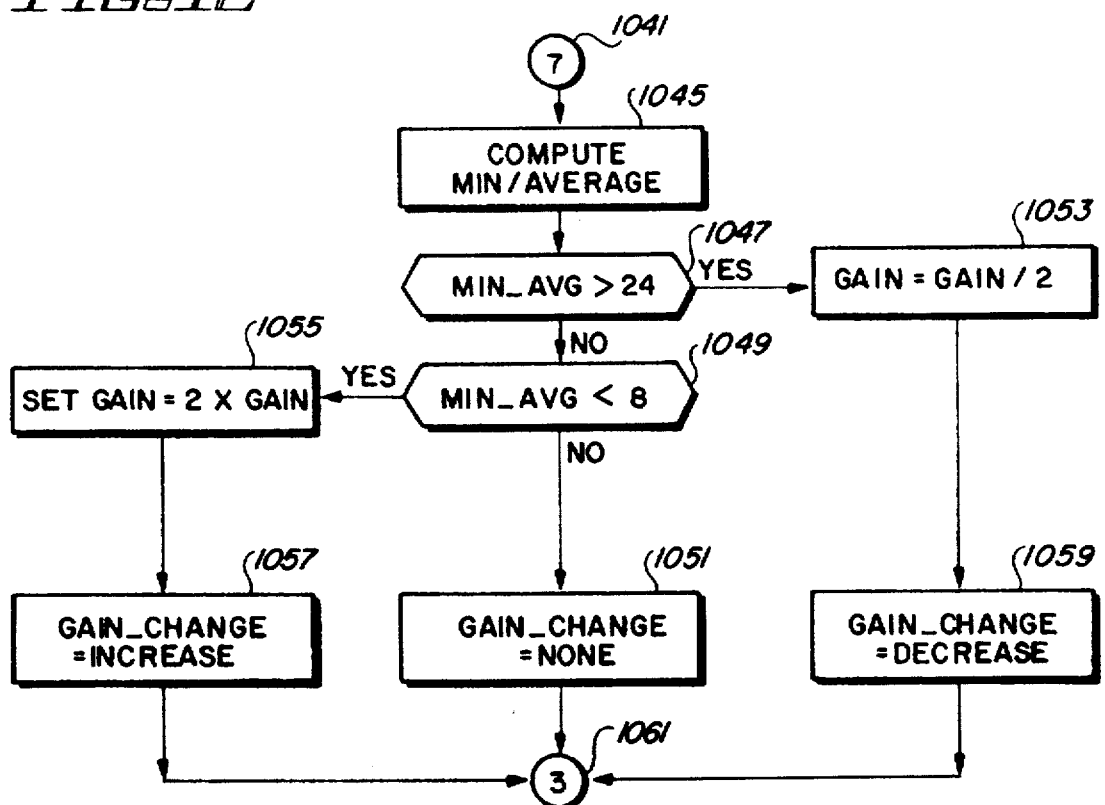

Note that the variable MIN_AVERAGE is similarly generated and used to generate the threshold value if the current polarity variable is negative (FIG. 11). Execution continues at Block 1097 (FIG. 12). The set THRESHOLD is then used by the threshold detector 38 as described previously. That is, the THRESHOLD value is written to the threshold detector 38 as a threshold set signal (Block 1063, FIG. 9), and execution of the control program terminates (Block 1065) until another event sensed signal is coupled to the microcontroller or until a cycle time-out signal is received.

Figure 9:
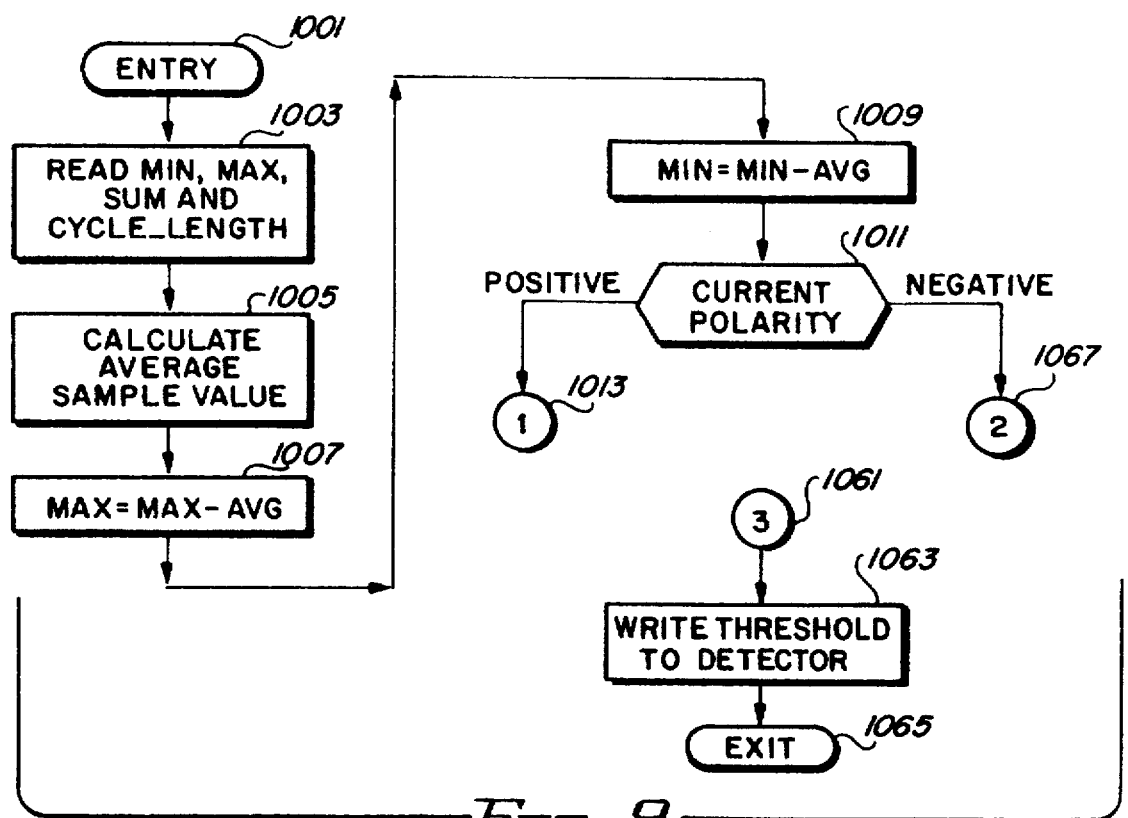
FIGS. 9, 10, 11, 12 and 13 are a flowchart of an exemplary control program that may be used by a microcontroller that is part of the cardiac threshold detector of FIG. 6.

Prior to writing the THRESHOLD value to the event detector, an arrhythmia flag value is generated by dividing the maximum value (or peak value) by the average baseline value (Block 1101) (FIG. 12). The arrhythmia flag value may be used, e.g., by a defibrillation program to set an arrhythmia flag signal, or otherwise determine whether or not high energy shock therapy should be delivered to the heart. Next, the variable MAX_AVERAGE is tested. If MAX_AVERAGE is greater than twenty-four (Block 1103) then the gain of the amplifier is decreased by one-half (Block 1109) and the variable GAIN_CHANGE is set to "DECREASE" (Block 1115). If MAX_AVERAGE is less than eight (Block 1105), then the gain of the amplifier is doubled (Block 1111) and the variable GAIN_CHANGE is set to "INCREASE" (Block 1113). If the MAX_AVERAGE is between twenty-four and eight, the variable GAIN_CHANGE is set to "NONE" (Block 1051). (NOTE: For a 5 bit A/D converter which has a possible 0–31 conversion codes, clipping would occur at conversion code 31 and no signal correlates to conversion code 0. Thus, conversion code 8 and 24 are chosen in Blocks 1103, 1105 as arbitrary limits to determine if the signal is within an optimum dynamic range.) Execution of the control program then continues at Block 1061 (FIG. 9). The GAIN_CHANGE variable is used by the pre-amplifier 42 to set its gain, as described previously.

As mentioned above, similar operation of the control program is exhibited in the event that the current polarity is negative. The primary difference in the execution of the control program when the current polarity is negative is that the minimum value is used to generate the variable MORPH_CHANGE and the threshold value (Blocks 1069 through 1091 of FIG. 11); and to generate the variable GAIN_CHANGE, and set the gain of the amplifier (Blocks 1045 through 1061 of FIG. 13).

The table, below, summarizes the signals used to indicate a change from rhythmic to arrhythmic cardiac activity, and vice versa. For example, if the peak R-wave signal divided by the average baseline is less than a prescribed threshold, then normal sinus rhythm is present. However, once it exceeds a prescribed threshold, then there is a high confidence level that an arrhythmia is present. Similarly, if the morphology change value, POLARITY, is set (indicating that the average amplitude of an R-wave has reversed polarity), or if there is an INCREASE or DECREASE in amplitude, or a GAIN change, then there is a high confidence level that R-waves are now being generated from a new, ectopic, location. Thus, the present invention indicates to the microcontroller that an arrhythmia is present. Furthermore, combinations of these morphology change signals can be used together, or in combination with conventional detection methods (e.g., tachycardia rate threshold, sudden onset, stability, etc.) to produce even higher confidence levels that an arrhythmia has begun.

| AVG. BASELINE | <threshold value | Normal rhythm |
| --- | --- | --- |
| AVG. BASELINE | >threshold value | arrhythmia present |
| PEAK + AVG. BASELINE | <threshold value | Normal rhythm |
| PEAK + AVG. BASELINE | >threshold value | arrhythmia present |
| morphology change value | POLARITY (changed) | arrhythmia present |
| morphology change value | INCREASED amplitude | arrhythmia present |
| morphology change value | DECREASED amplitude | arrhythmia present |
| morphology change value | GAIN (changed) | arrhythmia present |
| morphology change value | NONE (no change in amplitude, gain, or polarity) | Normal rhythm |

As described above, it is thus seen that the present invention provides a way of automatically adjusting the sensitivity (gain and/or threshold) of a cardiac event detection system in response to varying electrogram signals.

It is also seen that the invention provides implantable circuitry that inexpensively acquires information from an electrogram signal over a potentially long (e.g., infinite) period of time, without having to use external storage devices, e.g., magnetic tape recorders.

It is further seen that the invention provides an implanted system that advantageously acquires information from an electrogram signal without the need for large memories to store all or portions of the electrogram signal.

Additionally, it is seen that the invention provides an implantable arrhythmia detection system that generates output signals useable by an implantable therapy circuit, such as a pacemaker, cardioverter, or defibrillator, or the like, and that facilitates automatic control and adjustment of the therapy provided by such therapy circuit. Advantageously, it is seen that the output signals used to control the therapy circuit are readily generated without the need for performing complicated and highly power-consuming mathematical computations in an implanted microcontroller.

While the invention herein disclosed has been described by means of specific embodiments and applications thereof, numerous modifications and variations could be made thereto by those skilled in the art without departing from the scope of the invention set forth in the claims.

What is claimed is:

1. An implantable cardiac stimulation device for detecting arrhythmic cardiac activity in a heart and for delivering a therapy in response thereto, the system including an implantable lead that transmits an intracardiac electrogram signal from the heart, the system comprising:

sensing means, coupled to the lead, for sensing a plurality of characteristics of the intracardiac electrogram signal, the sensing means including:

event detecting means for detecting the occurrence of a cardiac event in the intracardiac electrogram signal;

peak detecting means for detecting a peak value of the cardiac event in the intracardiac electrogram signal;

means for determining an average baseline value for a prescribed portion of the intracardiac electrogram signal;

a minimum detecting means for detecting a minimum value of the intracardiac electrogram signal, the minimum value being the most negative value below the baseline value;

a maximum detecting means for detecting a maximum value of the intracardiac electrogram signal, the maximum value being the most positive value above the baseline value; and processing means for determining at least one of a plurality of morphology changes and for producing as an output an arrhythmia flag, thereby providing an indication of the presence of pathological arrhythmic cardiac activity in the heart, the plurality of morphology changes including:

a prescribed increase in the average baseline value;

a quotient of the peak value divided by the average baseline in excess of a prescribed threshold;

a change in polarity in one of the maximum value and the minimum value; and a prescribed change in amplitude in one of the minimum value, the maximum value, and the peak value; and therapy means, in response to the generation of the arrhythmia flag, for delivering therapeutic stimulation pulses to the patient's heart when pathological arrhythmic cardiac activity is detected.

2. An implantable cardiac arrhythmia detection system for detecting the presence of rhythmic and arrhythmic cardiac activity in a heart, the system including an implantable lead that transmits an intracardiac electrogram signal from the heart, the system comprising:

sensing means, coupled to the lead, for sensing a plurality of characteristics of the intracardiac electrogram signal, the sensing means including:

event detecting means for detecting the occurrence of an R-wave in the intracardiac electrogram signal;

means for determining an average baseline value for a prescribed portion of the intracardiac electrogram signal;

peak detecting means for detecting a peak value of the R-wave; and means for determining the quotient of the peak value divided by the average baseline value and producing as an output an arrhythmia flag whenever the quotient exceeds the prescribed amount, wherein a change in the quotient less than the prescribed amount indicates rhythmic cardiac activity and a change in the quotient greater than the prescribed amount indicates the presence of pathological arrhythmic cardiac activity in the heart.

3. In combination with an implantable stimulation device, a cardiac arrhythmia detection system for detecting the presence of rhythmic and arrhythmic cardiac activity in a heart, the system including an implantable lead that transmits an intracardiac electrogram signal from the heart, the improvement comprising:

sensing means, coupled to the lead, for sensing a plurality of characteristics of the intracardiac electrogram signal, the sensing means including:

event detecting means for detecting the occurrence of an R-wave in the intracardiac electrogram signal;

means for determining a baseline value for a prescribed portion of the intracardiac electrogram signal;

peak detection means for detecting a peak value of the R-wave; and arrhythmia detection means for detecting an arrhythmia based on an output signal which is a function of the peak value of the R-wave and the baseline value and for setting an arrhythmia flag whenever the output signal exceeds a prescribed threshold; and therapy means, in response to the arrhythmia flag, for delivering therapeutic stimulation pulses to the patient's heart.

4. The improved device, as set forth in claim 3, wherein the arrhythmia detection means comprises:

means for determining as the output signal the quotient of the peak value of the R-wave divided by the baseline value and the arrhythmia flag whenever the quotient exceeds the prescribed threshold.

5. The improved device, as set forth in claim 3, wherein the peak detection means comprises:

a minimum detecting means for detecting a minimum value of the intracardiac electrogram signal, the minimum value being the most negative value below the baseline value;

a maximum detecting means for detecting a maximum value of the intracardiac electrogram signal, the maximum value being the most positive value above the baseline value; and means for comparing an absolute value of the minimum value with an absolute value of the maximum value and for defining the peak value as the absolute value of the minimum value or the maximum value, whichever is larger.

6. The implantable cardiac stimulation system, as set forth in claim 3, further comprising:

averaging means for determining an average peak R-wave value and an average baseline value for use by the arrhythmia detection means;

means for detecting a change in morphology of the R-wave corresponding to R-waves being generated from an alternate conduction site; and reset means, responsive to a detected change in morphology, for resetting the averaging means so that a new average peak R-wave value and a new average baseline value can be computed.

7. The implantable cardiac stimulation system, as set forth in claim 6, wherein the means for detecting a change in morphology comprises:

amplitude detecting means for detecting an amplitude value of the R-wave; and means for detecting a change in amplitude between a current R-wave amplitude value and the average peak R-wave value.

8. The implantable system of claim 6, wherein the means for detecting a change in morphology comprises:

polarity detecting means for detecting a polarity value of the R-wave; and means for detecting a change in polarity of the current R-wave and a previous R-wave.

* * * * *